United States Patent [19]

Milroy et al.

[11] Patent Number: 5,376,889
[45] Date of Patent: Dec. 27, 1994

[54] SYSTEM AND METHOD FOR DETECTING AND LOCATING FLAWS ON OR BENEATH A SURFACE

[75] Inventors: William W. Milroy, Playa del Rey, Calif.;

[73] Assignee: Hughes Aircraft Company, Los Angeles, Calif.

[21] Appl. No.: 44,912

[22] Filed: Apr. 8, 1993

Related U.S. Application Data

[63] Continuation of Ser. No. 774,773, Oct. 10, 1991, abandoned.

[51] Int. Cl.$^5$ .............................................. G01R 27/04
[52] U.S. Cl. ................................. 324/644; 324/632; 324/642; 324/533; 73/601; 73/628
[58] Field of Search ................ 73/628, 601; 324/533, 324/632, 635, 648, 644

[56] References Cited

U.S. PATENT DOCUMENTS

| 3,710,243 | 1/1973 | Keenan | 324/632 |
| 3,715,667 | 2/1973 | Nicolson | 324/632 |
| 3,753,086 | 8/1973 | Shoemaker | 324/533 |
| 4,123,703 | 10/1978 | Robinson | 324/632 |
| 4,354,388 | 10/1982 | Diepers | 73/628 |
| 4,509,369 | 4/1985 | Kuljis | 73/628 |
| 4,520,308 | 5/1985 | Rohde | 324/632 |
| 4,634,963 | 1/1987 | Lunden | 324/632 |
| 5,185,579 | 2/1993 | Mertens | 324/533 |

FOREIGN PATENT DOCUMENTS

| 0142554 | 9/1982 | Japan | 324/644 |
| 0185151 | 8/1987 | Japan | 324/632 |
| 1160337 | 6/1985 | U.S.S.R. | 324/533 |

OTHER PUBLICATIONS

Tiuri: "A microwave instrument for measurement of small in homogenerties . . . "—Journal of Microwave Power—Jun. 1974.

Primary Examiner—Kenneth A. Wieder
Assistant Examiner—Jose M. Solis
Attorney, Agent, or Firm—L. A. Alkov; W. K. Denson-Low

[57] ABSTRACT

A parallel plate transmission line (20) is formed by conformal application of one or more dielectric and conductive layers to the surface under test (70). A signal generator (42) is employed to transmit variable frequency signals (60) along the transmission line (20). Discontinuities in the transmission line (20) cause reflections (62) which are received by a receiver (48). A processor (44) coupled to the signal generator (42) and receiver (48) detects and locates the discontinuities.

10 Claims, 6 Drawing Sheets

SYSTEM AND METHOD FOR DETECTING AND LOCATING FLAWS ON OR BENEATH A SURFACE

This is a continuation of application Ser. No. 07/774,773 filed Oct. 10, 1991, now abandoned.

BACKGROUND OF THE INVENTION

1. Field of the Invention

This invention relates to a system and method for determining the location of flaws and discontinuities on or beneath a surface and, more particularly, to a system and method for locating flaws and discontinuities on or beneath a surface using parallel plate regions and time domain reflectometry.

2. Description of Related Art

The surfaces of many vehicles and structures require systems to detect and locate flaws and discontinuities such as cracks, holes, corrosion and hidden voids so that the vehicle or structure's surface can be repaired and its performance level maintained. Structures such as oil platforms, bridges and dams, and vehicles such as automobiles, aircraft, spacecraft, ships and submarines are examples where such systems are useful.

The prior art can be classified generally into four basic technologies: ionizing radiation, acoustic, visible/infra-red, and eddy-current. Ionizing radiation techniques take "XRays" of the surface to detect discontinuities, and require extensive set-up and safety procedures. Therefore, these techniques are not suitable for real-time monitoring of surfaces. Acoustic techniques require introducing acoustic waves into the surface and measuring reflections from discontinuities present in the surface. These techniques are not suitable in high noise environments, nor in applications requiring low acoustic signatures. Additionally, detection sensitivity and range resolution are limited by the dispersive nature of acoustic waves in typical surfaces. Visible/infra-red techniques usually require special dyes that enhance visibility of the surface discontinuities in the visible or infra-red spectrum. These techniques require open access to the surface under test and are not practical for large structures or vehicles. Moreover, these techniques require experienced technicians to interpret the results and are not suitable for real-time monitoring. Eddy-current techniques use a probe to detect changes in the electric field generated by an electric current carried by the surface. Discontinuities in the surface cause perturbations in the field which are detected by the probe. These techniques also require open access to the surface and are most practical for inspecting small, accessible areas.

The present invention is directed to solving one or more of these problems.

SUMMARY OF THE INVENTION

Pursuant to the present invention, a parallel plate transmission line is formed by conformal application of one or more dielectric and conductive layers to the surface under test. A signal generator is employed to transmit variable frequency signals along the transmission line. Discontinuities in the transmission line cause reflections which are received by a receiver. A processor coupled to the signal generator and receiver detects and locates the discontinuities.

BRIEF DESCRIPTION OF THE DRAWINGS

The various advantages of the present invention will become apparent to those skilled in the art after studying the following specification and by reference to the drawings in which.

DESCRIPTION OF THE PREFERRED EMBODIMENT

Figure 1:
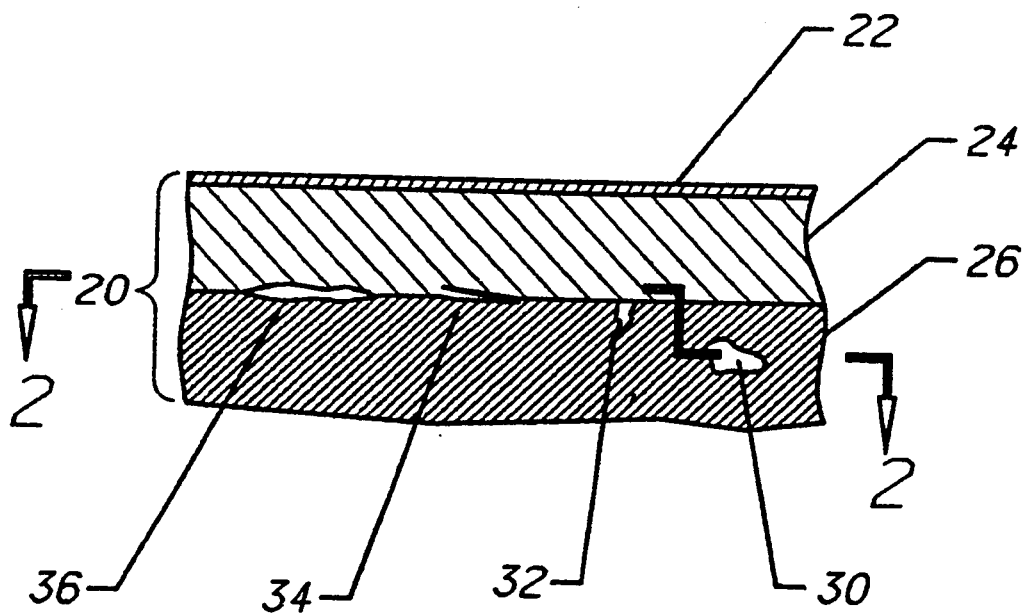
FIG. 1 is a cross-sectional view of one application where the present invention is used.
Figure 2:
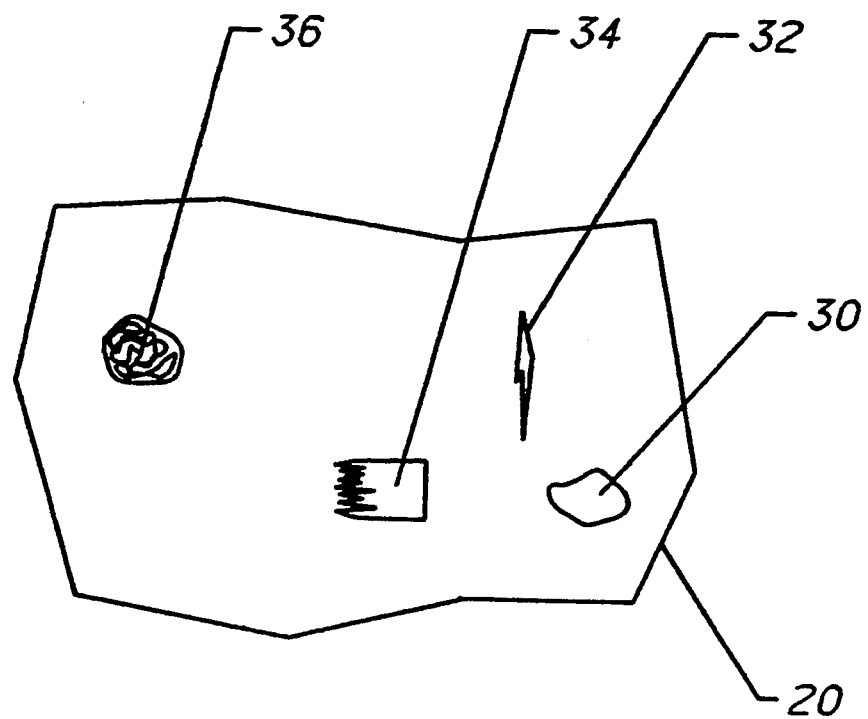
FIG. 2 is a top view of the application depicted in FIG. 1 taken along cut 2—2.

FIG. 1 illustrates one application where the present invention is used. A parallel plate transmission line structure 20 is formed out of a conductive layer 22, a dielectric layer 24, and another conductive layer 26. In this application, the conductive layer 26 is the surface under test and contains several common discontinuities. The discontinuities depicted are void 30, crack 32, delamination 34, and corrosion 36. FIG. 2 is a top view of conductive layer 26 shown in FIG. 1. Void 30 is visible in this view because a portion of cut 2—2 is taken beneath the surface (see FIG. 1). The parallel plate transmission line can be formed by adhesive lamination, plating, or spraying conductive and dielectric layers on the surface under test.

Figure 3:
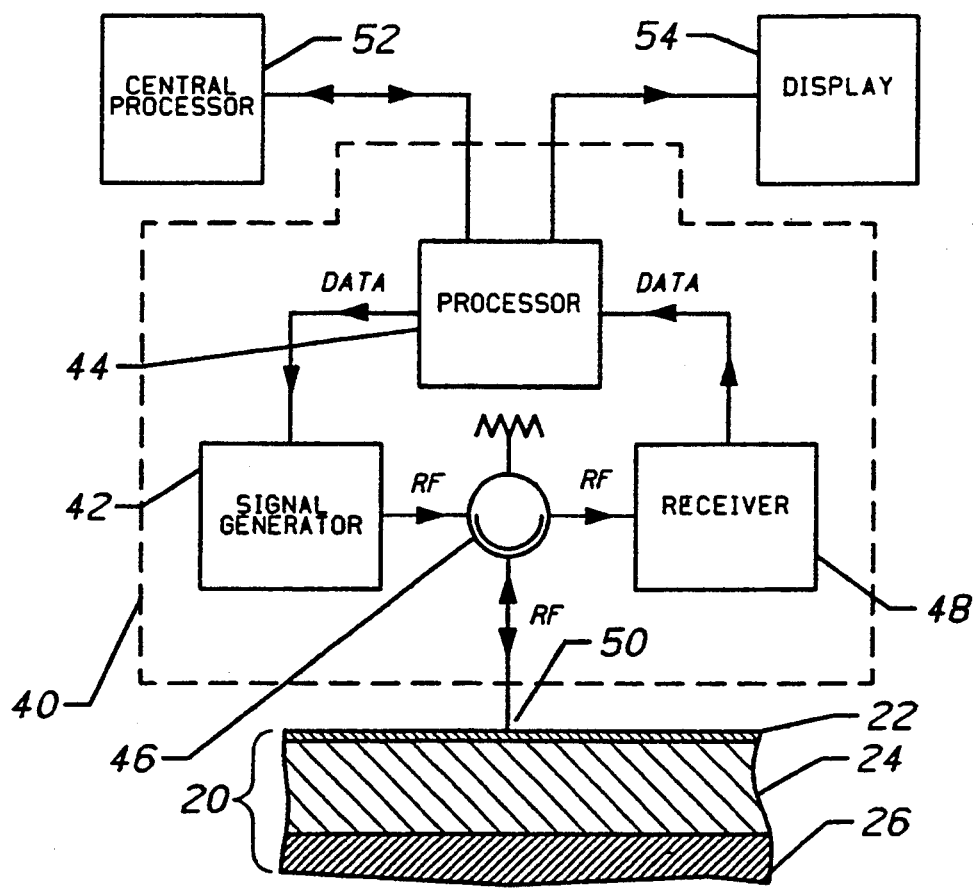
FIG. 3 is a functional block diagram of an integrated node made in accordance with the teachings of the preferred embodiment of this invention.

The structure of the main building block of the present invention is shown in FIG. 3. FIG. 3 is a functional block diagram of an integrated node 40. The signal generator 42, controlled by processor 44, provides calibrated RF signals swept in frequency over a broad bandwidth. These RF signals are channelled by a circulator 46 to the parallel plate transmission line 20 via transition point 50. In this application, the parallel plate transmission line 20 is composed of a conductive surface under test 26, a dielectric layer 24 and another conductive layer 22. Reflections from discontinuities are propagated back to the integrated node 40, through transition point 50 and circulator 46, and then to receiver 48. Integrated node 40 can be networked with a central processor 52, or display 54.

Figure 5:
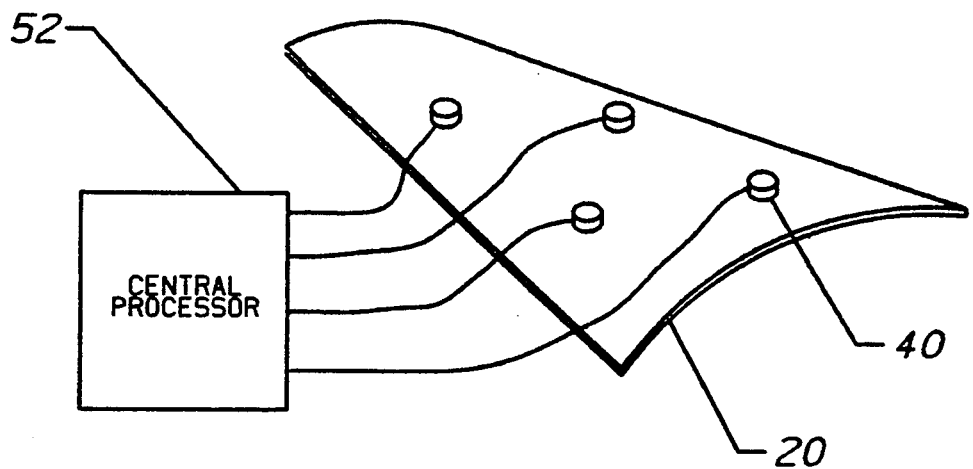
FIG. 5 is a partial plan view of one application with a plurality of integrated nodes coupled to a surface to be monitored.

A plurality of integrated nodes can be networked to monitor a large surface. FIG. 5 is a diagram showing a system with a plurality of integrated nodes 40 networked with a central processor 52 to monitor a surface. Integrated nodes 40 are placed to monitor the entire surface, the distance separating the integrated nodes 40 being such that any point on the surface 20 is within the detection range of at least three integrated nodes 40.

Figure 4:
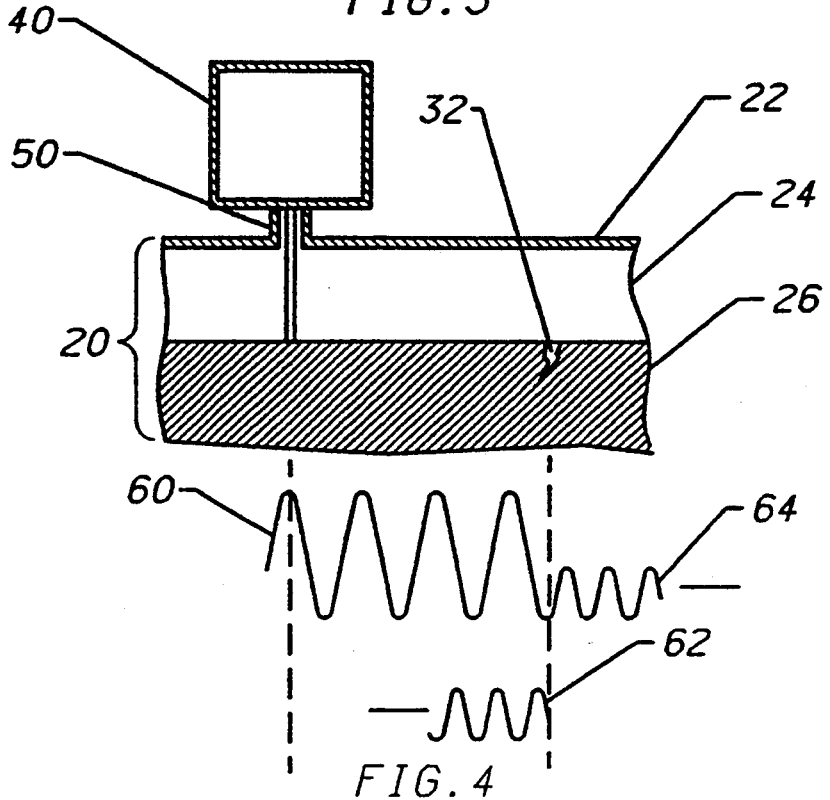
FIG. 4 is a cross-sectional view of a system made in accordance with the teachings of the present invention depicting the manner in which a wave is reflected from a discontinuity in a conductive surface.

FIG. 4 illustrates how reflections from discontinuities in the parallel plate transmission line 20 arise. Integrated node 40 injects original signal 60 into the parallel plate transmission line 20 via transition point 50. The original signal 60 propagates radially out in all directions from the transition point 50, but is depicted travelling in one direction for clarity. When original signal 60 reaches crack 32 in the surface under test 26, some of the energy from the original signal 60 is reflected back toward the integrated node 40 in the form of a reflected signal 62. The rest of the energy continues outward in the transmitted wave 64 and can be reflected by other discontinuities in the parallel plate transmission line 20.

The present invention operates as follows: each integrated node 40 propagates signals along the parallel plate transmission line 20 using its signal generator 42. Reflections from discontinuities are received by receiver 48. Receiver 48 provides phase, amplitude, and frequency data of the reflections to the processor 44. The processor 44 calculates the reflection coefficient and determines the range radius of the discontinuity using time domain reflectometry. The processor 44 can also store initial baseline signatures of reflections and compare them to signatures taken later. This technique simplifies monitoring by subtracting out expected reflections from edges, fasteners, etc.

Figure 6:
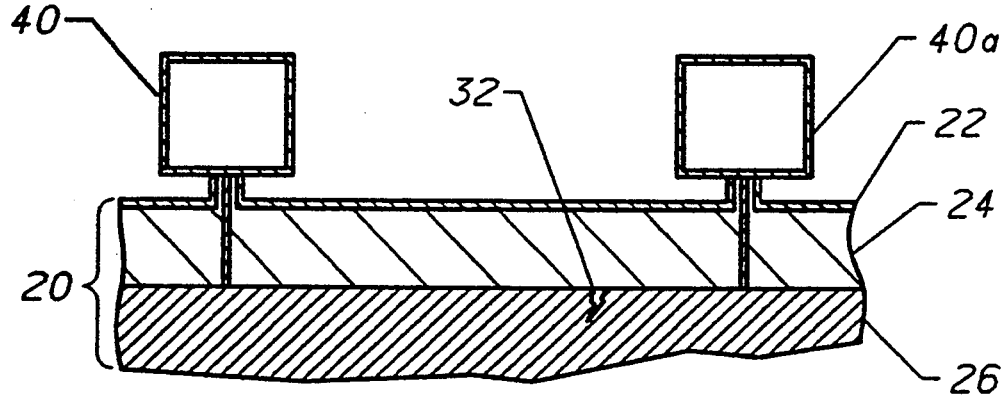
FIG. 6 is a cross-sectional view of an application depicting two integrated nodes.
Figure 7:
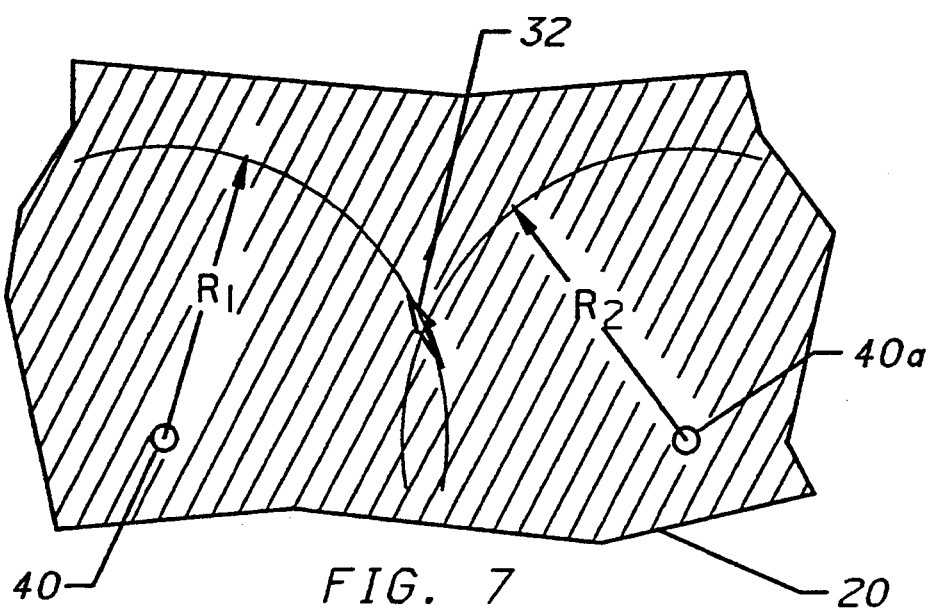
FIG. 7 is a top view of the application shown in FIG. 6.

Each integrated node 40 provides the range radius and reflection coefficient of each discontinuity it can detect. The central processor 52 determines the location of each discontinuity by multi-lateral triangulation. FIG. 6 illustrates the triangulation method using two integrated nodes 40 and 40a for clarity. The central processor determines the intersection of the range radii to determine the location of crack 32 as depicted in FIG. 7.

Figure 8:
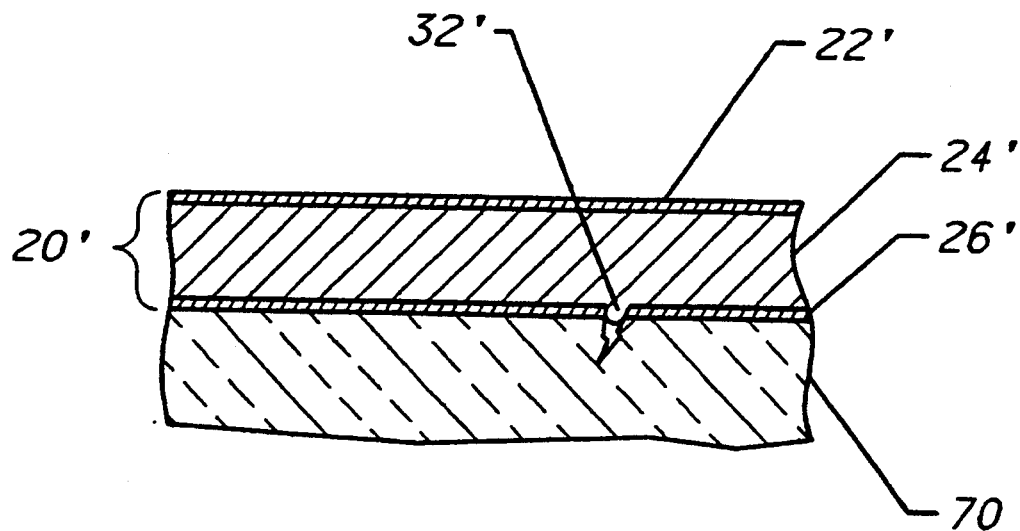
FIG. 8 is a cross-sectional view of an application depicting a transmission line conformally attached to a non-conductive surface.

FIG. 8 illustrates how the present invention would be used on a non-conductive surface 70. A parallel plate transmission line 20' is conformally attached to the non-conductive surface under test 70. This can be done by adhesion or deposition of the layers of the parallel plate transmission onto the non-conductive surface. Conductive layer 26' is made of a fragile material so that it will be discontinuous at the points the non-conductive surface 70 is discontinuous. FIG. 8 shows the surface under test containing a crack 32, and the conductive layer 26' broken at the same point. The crack 32 is detected and located as described above.

Figure 9:
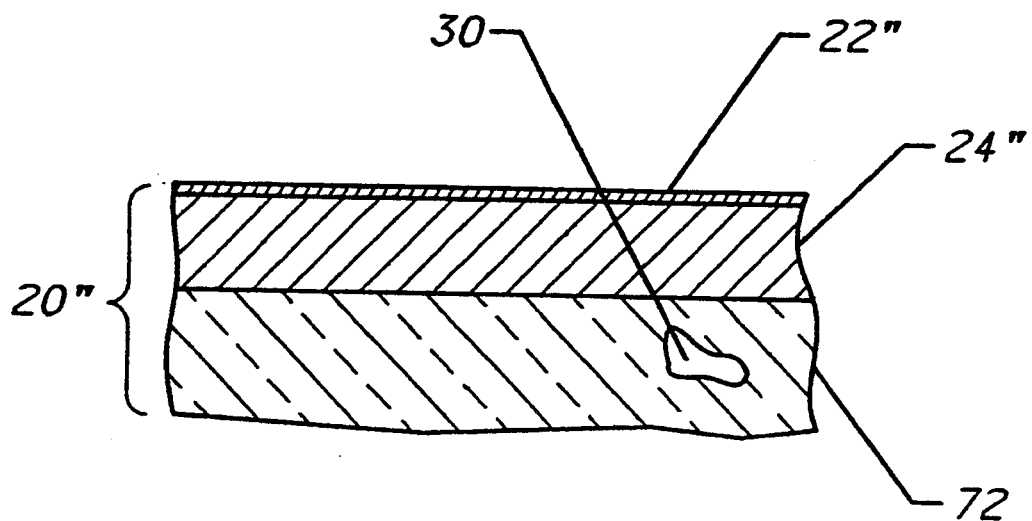
FIG. 9 is a cross-sectional view of an application depicting a void in a lossy conductor.

The present invention can also be used to detect flaws in poorly conductive surfaces such as the composite materials now used in many aircraft applications. FIG. 9 shows how the present invention is used on poorly conductive layer 72 to detect void 30. Voids can form in composite materials subjected to large electrostatic discharges such as might be expected if lightning were to strike an aircraft made of composite materials. The poorly conductive material 72 allows electromagnetic fields to penetrate it when propagating signals on the parallel plate transmission line 20", which in this embodiment, is formed by conformally applying conductive layer 22" and dielectric layer 24" to layer 72. Void 30 will cause a perturbation in the penetrating electromagnetic field, which result in reflections that can be detected as discussed previously.

Figure 10:
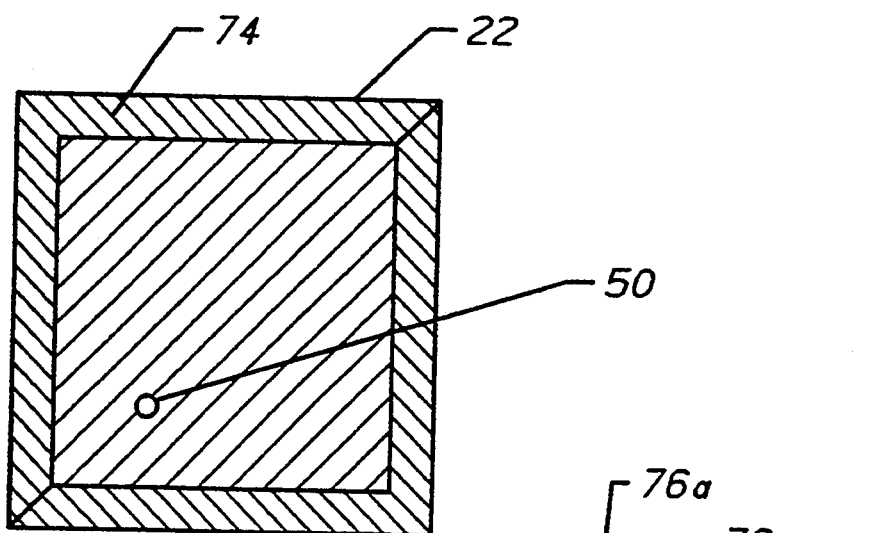
FIG. 10 is a top view of a lower conductive layer used in one application of the present invention.
Figure 11:
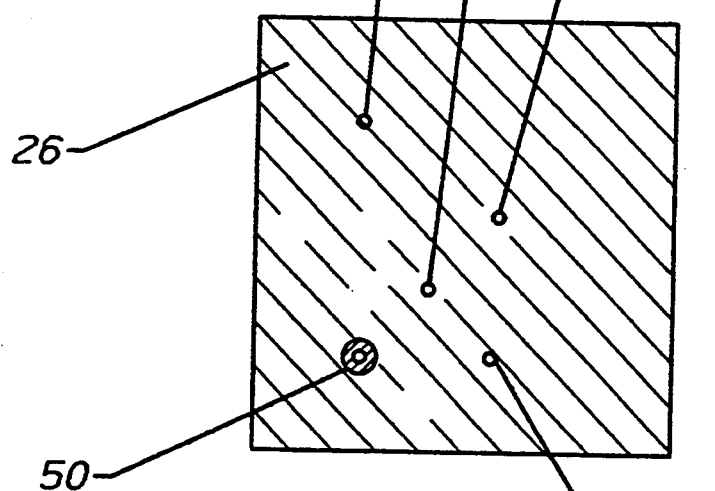
FIG. 11 is a top view of an upper conductive surface under test used in the application of FIG. 10.
Figure 12:
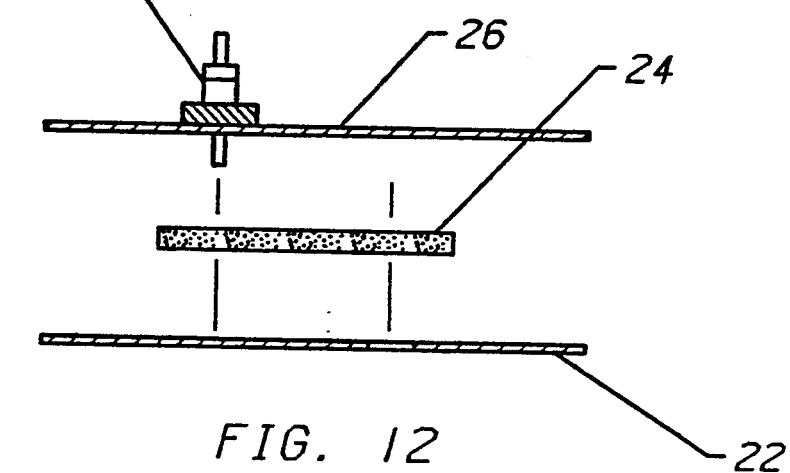
FIG. 12 is an exploded view of the application of FIGS. 10 and 11.

FIGS. 10, 11, and 12 show one embodiment of a system made in accordance with the present invention. A 12 inch square parallel plate transmission line was constructed out of 0.050 inch aluminum sheet stock and 0.100 inch low density foam. The low density foam was used as dielectric layer 24. FIG. 10 is a drawing of lower conductive layer 22. Lower conductive layer 22 was lined with high permeability absorber 74, 0.050 inch thick. The absorber 74 was attached in 1.5 inch wide strips to the perimeter of lower conductive layer 22 to reduce reflections. Transition point 50 was a standard SMA connector. FIG. 11 is a drawing of upper conductive layer 26, serving as the surface under test. Four 0.063 inch diameter holes, 76a, 76b, 76c, and 76d, were drilled in upper conductive layer 26 at different distances from transition point 50. Conductive pins, 0.050 inch in diameter, were selectively inserted in the holes to create discontinuities in upper conductive layer 26. FIG. 12 is an exploded view of the parallel plate transmission line showing how the layers were attached. Connection point 50 achieved an input reflection coefficient magnitude of less than 0.6 by using washers to roughly match impedance.

Figure 13:
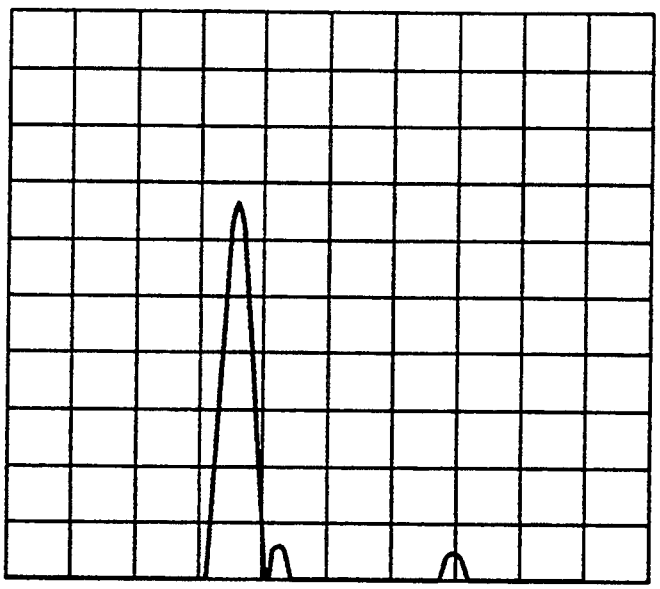
FIG. 13 is a graph of a measurement taken in the application of FIG. 12 with a single discontinuity present.
Figure 14:
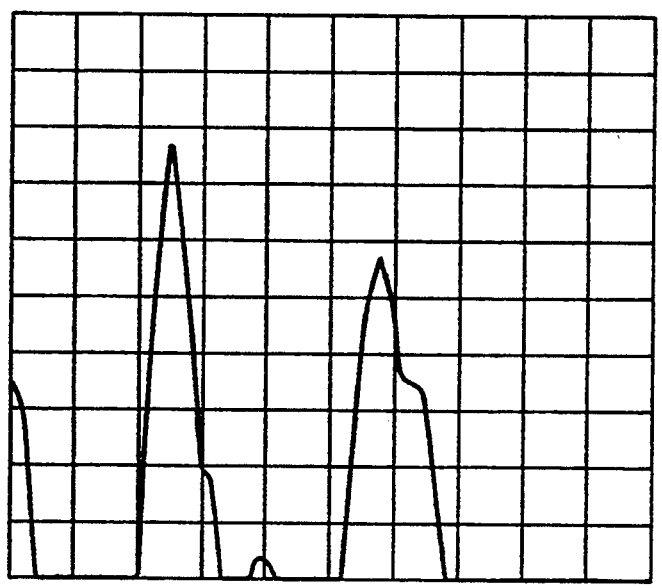
FIG. 14 is a graph of a measurement taken in application of FIG. 12 with two discontinuities present.

Discontinuities were detected as follows: A Hewlett Packard Vector Network Analyzer (Model HP 8720) served as the integrated node 40. With all the conductive pins removed, an initial baseline signature was recorded over the band 2 GHz to 20 GHz. Then one pin was inserted to create a discontinuity. The HP 8720 determined the reflection coefficient and range of a hole as shown in FIG. 13. As shown in FIG. 14, the HP 8720 also detected two discontinuities when conductive pins were inserted in two holes.

Thus, as described in the preferred embodiment, a parallel plate transmission line is formed on the surface to be tested and integrated nodes distributed across it. The integrated nodes, using time domain reflectometry, determine the reflection coefficient and range radius of each discontinuity it can detect. A central processor, networked with each integrated node, determines the location of the discontinuities by multi-lateral triangulation.

Conductive and dielectric layers can either be permanently or temporarily attached to the surface to form the parallel plate structure. For example, a weak adhesive can be used to temporarily attach the layers to the surface, allowing for easy removal once testing is completed. In another embodiment, the conductive and dielectric layers can be formed into a flexible mat that is detachable attached to a surface by simply placing it onto the surface and using gravity to hold it in place. In other applications, the layers can be detachably attached to the surface by fasteners such as screws or bolts.

This system has several advantages over the prior art. The parallel plate structure is inherently quiet, with no acoustic or RF emissions. Also, the parallel plate structure is insensitive to ambient noise and temperature, and has greater range per node compared to acoustic systems. Using broad bandwidths, time domain reflectometry techniques provide high resolution range and reflection amplitude information. Therefore, this system requires less hardware to monitor a surface and can provide greater long range resolution than acoustic systems.

Furthermore, the preceding description of the preferred embodiment was provided as an illustration of one manner in which to practice the invention. Design specific modifications, such as the varying the conductivity of the conductive layers, using multiple dielectric layers, or varying the thickness or dielectric constant of the dielectric layer, could be performed using ordinary skill in the art without departing from the spirit and scope of the invention.

What is claimed is:

1. A system for detecting and locating flaws and discontinuities in a conductive surface, the system comprising:
    a parallel plate transmission line formed by conformal application of at least one dielectric and conductive layers using the conductive surface to be tested as one of the plates of the parallel plate transmission line;
    generating means, coupled to the parallel plate transmission line, for generating calibrated RF signals swept in frequency over a broad bandwidth of variable frequencies and propagating them along said transmission line;
    receiving means, coupled to said transmission line, for receiving said RF signals generated by the generating means and reflected from discontinuities in said transmission line; and
    processing means, coupled to the generating means and receiving means, using time domain reflectometry triangulation for detecting and locating the position of the discontinuities on the conductive surface under test.

2. The system of claim 1 wherein said receiving means provides said processing means with the phase, amplitude, and frequency of the RF signals reflected from the discontinuities.

3. The system of claim 1 wherein said generating means and said receiving means are attached to at least three points on said transmission line.

4. The system of claim 1 further comprising means for detachably attaching dielectric and conductive layers to the surface under test to form said transmission line.

5. The system of claim 1 wherein one of the conductive layers of said transmission line is the surface under test.

6. The system of claim 1 wherein said transmission line is conformally attached to a non-conductive surface under test so that discontinuities in the surface cause discontinuities, at the same locations, in the conductive layer in contact with the surface.

7. The system of claim 1 further comprising display means, coupled to the processing means, for displaying the location of discontinuities in said transmission line.

8. The system of claim 1 further comprising circulator means, coupled to the generating means, receiving means and said transmission line, for coupling the generating means and receiving means to said transmission line at a single point; and
    the circulator means channels signals from the generating means to said transmission line, and signals from said transmission line to the receiving means.

9. The system of claim 1 wherein said processing means calculates the reflection coefficient and the range radius, from said generating means and said receiving means, of the discontinuities.

10. The system of claim 3 wherein said processing means calculates the position of each of the discontinuities by multi-lateral triangulation.

* * * * *